United States Patent [19]

Brown

[11] 4,095,180
[45] June 13, 1978

[54] METHOD AND APPARATUS FOR TESTING CONDUCTIVITY USING EDDY CURRENTS

[75] Inventor: Gordon Ralph Brown, Livonia, Mich.

[73] Assignee: K. J. Law Engineers, Inc., Detroit, Mich.

[21] Appl. No.: 644,809

[22] Filed: Dec. 29, 1975

[51] Int. Cl.² .............................................. G01R 33/12
[52] U.S. Cl. ..................................... 324/233; 324/243
[58] Field of Search ................ 324/34 TK, 40, 3, 6, 324/61 R, 67

[56] References Cited

U.S. PATENT DOCUMENTS

| | | | |
|---|---|---|---|
| 2,696,588 | 12/1954 | Criner | 324/40 |
| 3,020,470 | 2/1962 | Shawhan et al. | 324/3 |
| 3,278,839 | 10/1966 | Wells et al. | 324/40 |
| 3,337,796 | 8/1967 | Hentschel et al. | 324/40 |
| 3,418,572 | 12/1968 | Humphreys | 324/67 |
| 3,443,218 | 5/1969 | Jaggers et al. | 324/61 R |
| 3,443,219 | 5/1969 | Adams | 324/61 R |
| 3,443,220 | 5/1969 | Spademan | 324/61 R |
| 3,491,289 | 1/1970 | Petrini | 324/40 |
| 3,617,865 | 11/1971 | Hakata | 324/67 X |
| 3,706,029 | 12/1972 | Wandling et al. | 324/40 |
| 3,721,896 | 3/1973 | Mori et al. | 324/40 X |
| 3,764,897 | 10/1973 | Greenwood | 324/40 |
| 3,848,182 | 11/1974 | Gerner et al. | 324/40 |
| 3,904,957 | 9/1975 | Griese | 324/40 |
| 4,006,405 | 2/1977 | Greenwood et al. | 324/34 TK |

*Primary Examiner*—Gerard R. Strecker
*Attorney, Agent, or Firm*—Barnes, Kisselle, Raisch & Choate

[57] ABSTRACT

A method and apparatus for measuring conductivity of nonferrous metals using eddy current test principles in which conductivity is measured as a direct linear function of the period of the inducing signal at a preselected phase angle between the inducing and induced signals and is displayed directly in percentage of the International Annealed Copper Standard.

32 Claims, 3 Drawing Figures

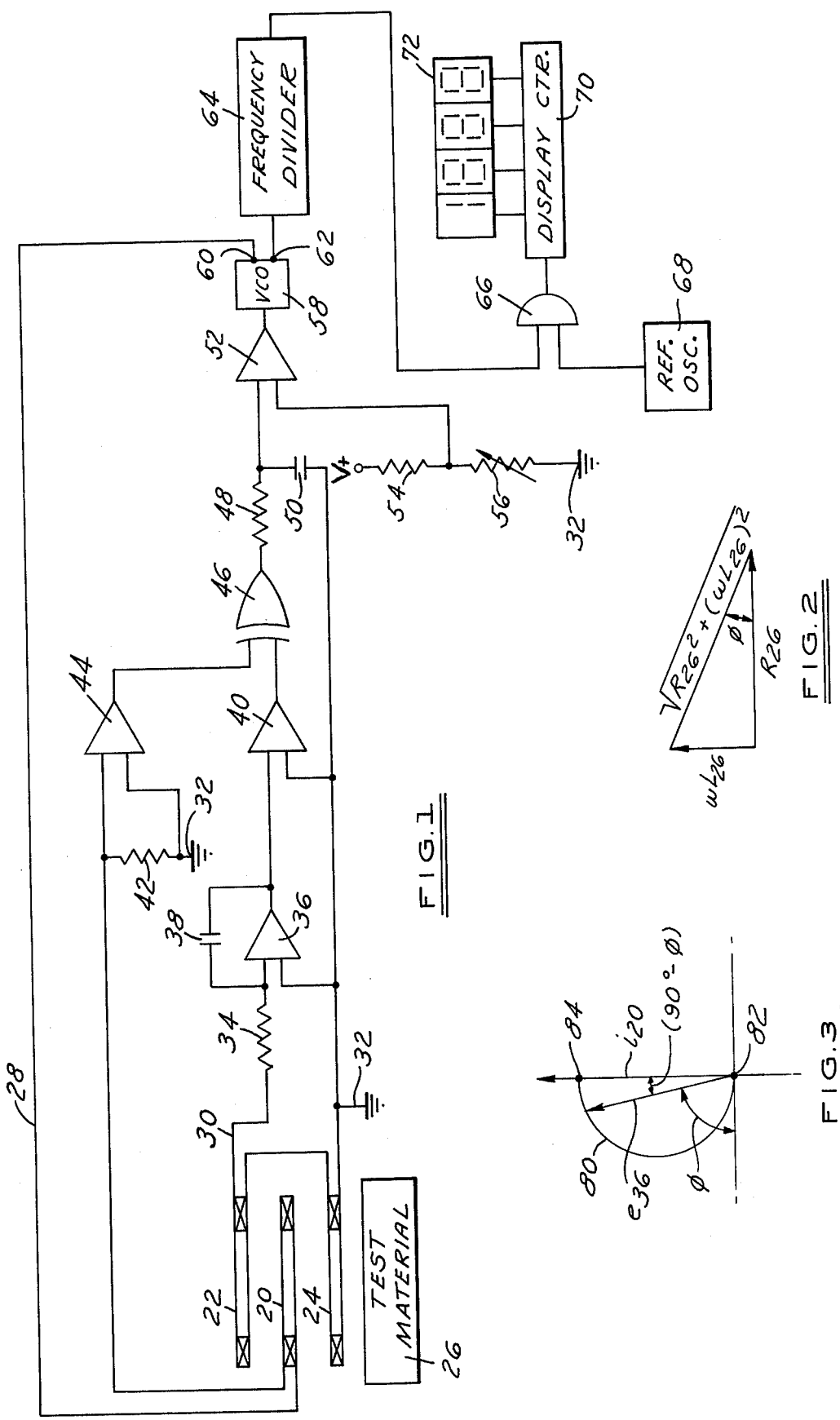

METHOD AND APPARATUS FOR TESTING CONDUCTIVITY USING EDDY CURRENTS

The present invention relates to conductivity test equipment and methods and, more particularly, to a method and apparatus for measuring the conductivity of nonferrous metals using an electromagnetic induction or eddy current principle.

Test equipment, including conductivity meters, which operates on an eddy current principle has been heretofore known and widely used in the nondestructive testing art. Briefly, in such equipment, a primary coil carrying an alternating current is placed near the material under test and induces an electromagnetic field in the material. When the material is conductive, the induced field causes eddy currents to flow therein having an amplitude and phase relationship to the inducing current which is a function of various material characteristics such as shape, cracks, flaws, permeability and conductivity. The eddy current so induced in the material gives rise to a second magnetic field which may be detected by a secondary pickup coil located near the material and which may be analyzed to determine test material properties.

Prior art conductivity meters using an eddy current principle generally attempt to measure the amplitude of the secondary magnetic field, i.e., the magnetic field induced by eddy currents, by placing the secondary pickup coil in a balancing bridge, for example. Opposing impedance arms of the bridge are then varied until the bridge is balanced; and the amplitude of the eddy current, which is related to conductivity, may then be determined. As will be shown in detail hereinafter, however, the amplitude of the induced voltage in the secondary coil varies directly, both with signal frequency and with inductive coupling between the coils and the test material. Hence the test frequency and the part-to-coil spacings must be closely maintained to achieve a reliable reading, both of which parameters are difficult to so maintain in actual practice. Furthermore, the conductivity scale for such an instrument is nonlinear and is inversely related to frequency. Moreover, such instruments must be recalibrated for each reading, for example, by initially "zeroing" the bridge. Conductivity readings are generally taken from dial indicators or meters associated with one or more impedance control arms and may require interpolation between adjacent graduations on one or more of the dials. Hence such devices require a skilled operator and tend to be bulky, difficult to operate, expensive and, most importantly, unreliable.

It is an object of the present invention to provide a method and apparatus for measuring conductivity of nonferrous metals using the above-described induced eddy current principle which can be implemented economically; which are reliable and provide consistently accurate measurements; which are easy to use; and/or which eliminate or at least substantially reduce the disadvantages and limitations of the aforementioned prior art techniques.

More specifically, it is an object of the present invention to provide an eddy current conductivity method and apparatus which have a greatly reduced sensitivity-to-electromagnetic coupling between the test coils and the part such that the invention may be advantageously used to determine the conductivity of test material having non-flat or uneven surface contours.

It is a further object of the present invention to provide a method and apparatus which will reliably determine the conductivity of a test material covered by a protective coating of paint or plastic, etc., and in which the otherwise detrimental effects of variations in coil/material coupling are reduced to such an extent that reliable readings may be obtained where the test coils are hand held in close proximity to the test material by an unskilled operator.

It is another object of the present invention to provide a method and apparatus which display measured conductivity directly in percentage of a selected standard, such as percentage of the International Annealed Copper Standard (% IACS), and/or are capable of providing conductivity measurements up to one percent IACS accuracy and 0.1 percent IACS resolution.

In accordance with the present invention, it has been discovered that, for nonferrous test materials having a predetermined minimum size with respect to the test coils, the conductivity of a test material may be measured as a direct linear function of the period of the inducing current at any given phase angle between inducing current and induced voltage. More specifically, conductivity of a nonferrous metal having a predetermined minimum size may be measured in accordance with the present invention by applying a periodic inducing signal to a primary coil located in proximity to the test piece, developing an induced signal as a function of the eddy currents induced in the material by the primary coil current, measuring the phase angle between the inducing and induced signals, varying the frequency of the inducing signal until the phase angle between the inducing and induced signal reaches a preselected value, measuring the period of the inducing signal at the frequency, and displaying the measured period as a scaled function of % IACS.

The novel features which are considered to be characteristic of the present invention are set forth in particular in the appended claims. The invention itself, however, together with additional objects, features and advantages thereof, will be best understood from the following description when read in conjunction with the accompanying drawings in which:

FIG. 1 is a schematic diagram of an exemplary but presently preferred embodiment of the eddy current conductivity meter provided in accordance with the present invention;

FIG. 2 is a vector diagram depicting the impedance characteristics of a test material; and FIG. 3 is a polar vector diagram useful in understanding the principles and operation of the invention.

Referring to FIG. 1, a primary coil 20 and a pair of secondary coils 22, 24 are disposed as shown in close proximity to a test material 26. Primary coil 20 receives a periodic inducing current signal via conductor 28 and, in accordance with the well-known theory outlined above, eddy currents are induced in material 26 as a function, among other properties, of the material conductivity. Secondary coils 22, 24 are so disposed with respect to coil 20 and are connected to each other in a manner as to produce between secondary coil output line 30 and common bus or circuit ground 32 a differential voltage signal which varies as a function of the electromagnetic field generated by eddy currents in material 26 but independently of any direct coupling between the primary coil 20 and the secondary coils 22, 24.

The induced signal on line 30 is fed to an integrator comprising a resistor 34, an amplifier 36 and a capacitor 38 to develop an output which varies as an integral function of the induced voltage signal on line 30. The output of integrating amplifier 36 is fed to a switching amplifier 40 which provides at its output a square wave signal at the frequency of the induced voltage signal in coils 22, 24 and lagging 90 degrees with respect thereto. Coil 20 is connected through a resistor 42 to ground 32 to convert the inducing current signal to a voltage which is applied to the input of a switching amplifier 44 whose output is a square wave signal at the frequency and phase angle of the inducing signal in coil 20.

The outputs of switching amplifiers 40, 44 are connected to respective inputs of a phase detector comprising an exclusive-OR (EOR) gate 46 which has its output serially connected through a resistor 48 and a capacitor 50 to ground 32. The output of gate 46 is low or a logical zero when the respective outputs of amplifiers 40, 44 are the same (low or high) and is high or a logical one when the respective outputs of amplifiers 40, 44 are different. Resistor 48 and capacitor 50 act as a low pass filter to provide across the capacitor a DC analog signal whose amplitude is proportional to the duty cycle of the output of gate 46 and hence proportional to the phase angle relationship between the induced and inducing signals represented by the outputs of amplifiers 40, 44, respectively. The phase relationship signal across capacitor 50 is fed to one input of an error amplifier 52 which receives its second or reference input from the center junction of a resistor voltage divider 54, 56 connected between a voltage V+ source and ground 32. Resistor 56 is made adjustable for factory setting of the reference input to amplifier 52 to a preselected level representative of a preselected phase relationship between the induced and inducing signals. The method of determining the reference level will be discussed in detail hereinafter.

The output of amplifier 52, which is indicative of the difference between the measured and desired phase relationship between the induced and inducing signals, is fed to a voltage-controlled oscillator 58 which provides buffered outputs 60, 62 as a function of the control signal from amplifier 52. Although the periodic output at 60, 62 may be a sinusoidal signal, it has been found that a periodic triangular or zigzag output signal may be generated less expensively than a pure sinusoidal signal and may be used in accordance with the present invention without any noted detrimental effect upon instrument accuracy. Output 60 is fed via conductor 28 to primary coil 20.

Oscillator output 62 is fed to a frequency divider 64 which (1) divides the oscillator output by a selected scaling factor to reduce the effect of noise and jitter on the output display, and (2) then divides the scaled frequency by two to provide a signal indicative of the period of the scaled frequency. Stated differently, frequency divider 64 comprises a first frequency divider to reduce the frequency of oscillator output 62 by a selected scaling factor and a second frequency divider to divide the output of the first divider by two and to thus yield a signal indicative of the period of the first divider output; i.e., high during the first period of the first divider output, low during the second period, high during the third period, etc. The output of frequency divider 64 is fed to one input of an AND gate 66 which receives a second input from a reference oscillator 68. Thus the output of gate 66 comprises the output of oscillator 68 gated by the output of frequency divider 64 and provides a measure or count of the period of oscillator output 62 divided by the scaling factor. The output of gate 66 is connected to a display counter 70 and associated seven-segment display 72 to provide a digital readout as a function of measured period.

Operation of the conductivity meter shown in FIG. 1 may be explained on a theoretical basis as follows. Current in the primary coil 20 may be expressed by the equation:

$$i_{20} = I \sin \omega t \qquad (1)$$

wherein $\omega$ is the excitation frequency expressed in radians per second. Although a triangular excitation current rather than a pure sine wave is presently preferred for economic reasons, as noted above, this has been found to make no noticeable difference in the results; and the theoretical calculations based upon the sine wave excitation signal originally conceived are still considered applicable for all practical purposes. The current induced in material 26 by the current in coil 20 may be expressed as follows:

$$i_{26} = \frac{\omega M_{20/26} I \cos \omega t}{R_{26} + j\omega L_{26}} \qquad (2)$$

wherein $R_{26}$ and $L_{26}$ are the resistance and inductance of material 26, respectively, $M_{20/26}$ is the mutual inductance or coupling between coil 20 and material 26, and $j$ is the imaginary unit vector equal to the square root of $-1$. Referring to FIG. 2, which is a vector diagram depicting the impedance characteristics of material 26, it will be seen that:

$$\phi = \tan^{-1} \frac{\omega L_{26}}{R_{26}} \qquad (3)$$

After appropriate factoring and substitutions, equation (2) may be reduced to:

$$i_{26} = \frac{\omega M_{20/26} I}{\sqrt{R_{26}^2 + (\omega L_{26})^2}} \cos(\omega t - \phi) \qquad (4)$$

The voltage induced in differentially connected coils 22, 24 and appearing between line 30 and ground 32 may be expressed as follows:

$$e_{30} = -\frac{\omega^2 M_{20/26} M_{26/22,24} I}{\sqrt{R_{26}^2 + (\omega L_{26})^2}} \sin(\omega t - \phi) \qquad (5)$$

wherein $M_{26/22,24}$ is the mutual inductance or coupling between material 26 and coils 22, 24. Although the voltage expressed by equation (5) may be used for purpose of conductivity analysis, it will be noted that the amplitude of the expression varies with the excitation frequency ($\omega$). To reduce the dynamic range of switching amplifier 40, phase detector gate 46, etc., the voltage expressed in equation (5) is integrated by amplifier 36 to yield:

$$e_{36} = -\frac{\omega M_{20/26} M_{26/22,24} I}{\sqrt{R_2 + (\omega L_{26})^2}} \cos(\omega t - \phi) \qquad (6)$$

If it were attempted to obtain a conductivity measurement by comparing the amplitudes of equations (1) and (6), the frequency ($\omega$) and the mutual coupling between the material and coils ($M_{20/26}$ and $M_{26/22,24}$) would have to be held constant. This is difficult to achieve in practice, however, particularly where the coils are to be embodied in a hand-held probe and the mutual coupling between the coils and material may vary widely with surface contour, surface coating or probe orientation, for example. In accordance with the present invention, it has been noted from equations (1) and (6) that, where the excitation current ($i_{20}$) varies with sin $\omega t$, the integrated secondary coil voltage ($e_{36}$) varies with cos ($\omega t - \phi$). Where the test material 26 is nonferrous, i.e., the relative permeability is equal to one, and where the test material is sufficiently large in the area of the probe, the inductance of material 26 ($L_{26}$) may be considered a geometric constant; or, stated differently, the inductance of the material may be considered constant for test samples having at least a predetermined minimum size. Generally, the minimum surface area and depth of the test material for which the above assumption is true depend upon the coil diameters and excitation frequency. Where the coils are about one-half inch in diameter and where the excitation frequency range is chosen to be 5 to 250 kilohertz, the minimum part size is about one inch in diameter by onetenth inch thick. The method for choosing the frequency range will be described in detail hereinafter.

Where $L_{26}$ may be regarded as constant as described above, equation (3) may be reduced to:

$$\omega/R_{26} = 1/L_{26} \tan \phi \qquad (7)$$

Where the phase angle at which the measurement is to be made is preselected and constant, equation (7) may be further reduced to:

$$f = \omega/2\pi = K^1 R_{26} \qquad (8)$$

wherein $K^1$ is a constant equal to $\tan \phi/2\pi L_{26}$. Converting frequency ($f$) to period (T), and resistance ($R_{26}$) to conductivity ($G_{26}$), equation (8) assumes the form:

$$G_{26} = K T \qquad (9)$$

wherein K is equal to $K^1$ times a factor related to the eddy current path in the material which, as noted above, is considered constant for materials having a predetermined minimum size and shape. Hence the conductivity of material 26 is a linear function of the excitation period (T) at a selected phase angle ($\phi$).

The assumption that material inductance ($L_{26}$) is constant is valid for coil/material spacing variations on the order of ten percent of the coil diameter. This allows the meter disclosed herein to operate on uneven surfaces, such as the outside wall of a cylinder, and through material coatings such as paint. Insensitivity to small probe position variations also renders testing with a hand-held probe more accurate and reliable.

FIG. 3 is a polar diagram which shows the relationship between the integrated coil voltage ($e_{36}$) and the inducing current ($i_{20}$) in nonferrous material of the above-mentioned predetermined size and shape. In FIG. 3, curve 80 is the locus of points defined by voltage vector $e_{36}$ set forth in equation (6) as the frequency ($\omega$) is swept from zero (point 82) toward infinity (point 84). The phase angle ($\phi$) as shown in FIG. 3 is measured in the second quadrant between vector $e_{36}$ and the horizontal; hence vector $e_{36}$ is displaced from vector $i_{20}$ by an angle of (90° $- \phi$).

From equation (9), it will be evident that the highest frequency (1/T) at which the instrument must operate will depend upon the lowest conductivity to be measured. The instrument frequency range is determined by the electronic components to be used therein. In an operating embodiment of the invention which measures two percent to one hundred percent IACS conductivity, a frequency range of five to two hundred fifty kilohertz was selected. The desired percentage conductivity range and the frequency range of VCO 58 determine the frequency of reference oscillator 68 and the division factor of divider 64. To exemplify, where it is desired to have display 72 read 100.0 for 100 percent IACS conductivity at an oscillator 58 frequency of five kilohertz, and to have a display of 2.0 at a frequency of 250 kilohertz, a convenient division factor is 2048 (i.e., a scaling factor of 1024 followed by an additional factor of 2) for which reference oscillator 68 would be set at a frequency of 4.883 KHz.

More generally, where divider 64 divides the frequency of oscillator output 62 by twice a selected scaling factor, the count shown at display 72 will be equal to the scaling factor multiplied by the ratio of the reference oscillator 68 frequency divided by the controlled oscillator 58 frequency. The percentage conductivity will be equal to the desired percentage resolution, in the disclosed embodiment 0.1 percent, times the figure in display 72.

Once the scaling factor of divider 64 and the frequency of oscillator 68 have been determined as described above, resistor 56 may be empirically calibrated to the desired phase angle reference signal as follows. The system is energized and the coils 20, 22 and 24 are placed in proximity to a test material of known conductivity, one hundred percent IACS, for example. The meter is then calibrated by merely adjusting resistor 56 until display 72 reads the known conductivity percentage, in this case, one hundred. Where the inductance ($L_{26}$) of the test material is known, the desired phase angle ($\phi$) may analytically be determined from equation (7) for a particular frequency ($\omega$) and conductance (1/$R_{26}$). For the embodiment herein described having a five to two hundred fifty kilohertZ frequency range and a 2 to 100 percent IACS measuring range, the phase angle ($\phi$) when the meter was calibrated as indicated above was about 74°. The value of resistance 56 may be then generally determined since the reference voltage to amplifier 52 will be equal to (90° $- \phi$)/180° or, in the example given, 16°/180° multiplied by the supply voltage. Even where the phase angle ($\phi$) is determined analytically, however, it is preferable to make resistor 56 factory adjustable to compensate for supply voltage and circuit operating tolerances, variations, etc.

It has been assumed in the foregoing discussion that all calibration and test measurements, etc., are being made at the IACS standard temperature of 20° C. It will be apparent, however, that the invention disclosed is equally useful at temperatures other than standard. In the case of measurements at other than standard temperature, the operator may relate measured conductivity to conductivity at standard temperature according to the following well known equation:

$$G_s = G_m(1 + \alpha \Delta T) \qquad (10)$$

wherein $G_s$ is conductivity under standard temperature conditions (20° C), $G_m$ is measured conductivity, $\alpha$ is the conductivity change v. temperature coefficient of the material in question and is readily available for most materials, and $\Delta T$ is the extent to which the measurement temperature departs from standard. It will be apparent that, where only one material will be measured and where such measurement will always be performed at the same temperature, the instrument may be recalibrated to compensate for the temperature differential. Similarly, where only one material will be measured, but at varying temperatures, appropriate temperature compensation circuitry may be incorporated into the meter. Moreover, where maximum versatility is required with respect to the material and temperature, the above-mentioned temperature compensation circuitry may be made operator programmable such that the temperature coefficient of a particular material may be entered, and such that the meter will provide a conductivity measurement which is automatically compensated to standard temperature.

From the foregoing description, it will be apparent that the conductivity meter disclosed fully satisfies all of the objects, features and advantages set forth herein. Although the invention has been described in conjunction with a specific embodiment thereof, modifications and variations thereto will suggest themselves to persons skilled in the art. For example, it was noted above for reasons set forth in detail that the inductance of test material 26 is considered to be a constant for material above a minimum size. However, the present invention may also be used on material samples of less than the minimum size by merely recalibrating the instrument on an actual sample of the desired size having a known conductivity. The instrument may then only be used on samples of that size but will still yield accurate results since sample conductivity is still a linear function of period. Only the constant K of equation (9) has been changed. The instrument may, of course, be recalibrated at any time for samples above the minimum size.

Similarly, in the embodiment of the invention herein disclosed, the reference phase angle ($\phi$) is factory calibrated by adjusting the input to error amplifier 52. However, inasmuch as phase angle and frequency are directly interrelated by equation (7), the reference input to error amplifier 52 could be set by fixed resistors or the like, and the instrument could be calibrated or "fine tuned" by adjusting the frequency of oscillators 58 or 68 to yield a particular display for a material sample of known conductivity. However, meters using this method of calibration would have different outputs from oscillator 58 and divider 64 for materials of the same conductivity. For reasons of standardization, the calibration technique disclosed in connection with FIG. 1 is preferred.

The disclosed scaling factor 1024 is convenient since frequency dividers of twice that figure, i.e., 2048, are readily available. From the foregoing discussion, however, it will be apparent that other scaling factors and/or reference oscillator frequencies may be used where desired. Moreover, it will be apparent that frequency divider 64 could be eliminated and the frequency of oscillator 68 increased accordingly. However, this arrangement eliminates the salutory filtering effect of divider 64 in helping to eliminate noise and display jitter, and hence is not preferred. Furthermore, it will be apparent that display counter 70 could be expanded to include several lower-order counting levels, with display 72 being connected to only the four most significant digits. Such an expanded display counter would combine the functions of both divider 64 and counter 70 of FIG. 1 and would also reduce noise and jitter, etc.

The particular display 72 shown in FIG. 1 is a four-digit display which provides accurate readings resolved to the third decimal place, i.e., to 0.1%IACS. It will be apparent that, where greater or lesser conductivity resolution is required, more or less display digits may be provided. Overall accuracy of the instrument and method herein disclosed varies according to the quality of components used, etc. However, because digital rather than analog techniques are used where possible and because the disclosed method eliminates the need for nonlinear calibrations, an instrument accuracy on the order of one percent may be achieved using standard inexpensive components. The method and meter herein disclosed is specifically adapted to provide conductivity measurements in percent IACS. It will be apparent, however, that the method is equally applicable and the meter may be readily adjusted to provide conductivity measurements as a percentage of any desired standard, such as a pure copper standard, for example, which is about one hundred three percent of corresponding IACS measurements.

In the specific embodiment described herein, the inducing and induced signals appear in separate coils, i.e., in coil 20 and in differentially connected coils 22, 24, respectively. It will be apparent, however, that the invention is equally useful with little or no modification in combination with other types of eddy current test coil arrangements known in the art. For example, the inducing and induced signals may be sensed as separate functions of the current and voltage appearing in a single coil, located in proximity to the test material and serving as both a primary coil and a pickup coil. In this situation, the single coil may be driven by a constant current source such that the voltage across the single coil varies as a function of the eddy currents in the test material while the current is not influenced by the test specimen. Other arrangements can also be used so that the eddy current effect can be isolated for phase comparison against a reference.

Useful indications of a characteristic of a test material might also be obtained by using differential comparison techniques wherein the eddy current test signal from a first test coil associated with a first unknown test specimen is compared against an eddy current test signal from a second test coil associated with a known or standard test specimen. As is conventional in other eddy current testing techniques, the first and second coils could be driven from a common source. The source frequency would then be varied until the two test signals have a predetermined phase relation therebetween and then the characteristic, such as conductivity, would be determined as a function of that frequency or period of the source signal yielding the predetermined phase angle. Of course, in this situation, the test signal from the known or standard test specimen serves as a reference signal for comparison against the test signal from the unknown test specimen and the known characteristics of the standard test specimen relate the phase of the reference signal to the phase of the signal in the first coil.

In light of the modifications discussed above, it should be apparent that the present invention broadly contemplates comparing an eddy current test signal that varies as a function of eddy currents in an unknown test specimen, e.g., the induced signal $e_{30}$ in coils 22, 24 (FIG. 1) against a reference signal to determine the phase relationship therebetween where the reference signal is not identical to the signal inducing the eddy currents, e.g., the inducing signal in coil 20 (FIG. 1), but where the reference signal is otherwise related in phase, directly or indirectly, to the inducing signal. In such a situation, the reference signal would be compared to the test signal that varies as a function of the eddy currents in the test material. The frequency or the period of the reference signal and the inducing signal yielding the predetermined phase angle could then be used to determine the desired characteristic, such as conductivity, of the material.

It will also be apparent that VCO 58 (FIG. 1) may be replaced by an operator-controlled variable frequency oscillator; and a meter or the like may be connected to the output of amplifier 52, whereby an operator may adjust the frequency of the oscillator until the meter is zeroed. However, such an arrangement does not readily lend itself to rapid measurements and introduces a needless source of error, i.e., the operator's visual interpretation of the meter reading. Accordingly, the "automated" arrangement shown in FIG. 1 is preferred. Moreover, it will be evident from examination of equations (1), (5) and (6) that the frequency ($\omega$) does not change as the induced and inducing signals are processed by the system of FIG. 1; or, stated differently, the various signals in the circuit are all at the same frequency. Accordingly, the frequency at which the meter is operating can be measured by connecting frequency divider 64 at various other points in the circuit other than directly at oscillator output 62. For example, divider 64 may be connected to the output of either of amplifiers 36, 40 or 44 or, for that matter, may be connected through an appropriate isolation circuit at differential coil output line 30.

The invention has been described in detail in connection with a particular selected phase angle and a certain frequency range. However, such specific details have been provided merely to illustrate the method for selecting such a parameter and for the purpose of understanding the invention which, in its broadest aspects, is not to be construed as being limited by any specifically disclosed parameters. Furthermore, although the invention has been disclosed as a method and apparatus for measuring conductivity of nonferrous metals, the principles of the invention may be potentially useful for analyzing characteristics of ferrous metals and for determining material characteristics other than conductivity. It will also be understood that although the meter measures conductivity, the meter is readily usable to determine material characteristics such as stress, flaws or fatigue which give rise to conductivity changes. The present invention would also be useful in a production line inspection station for accepting or rejecting parts according to their conductivity or other characteristic in a manner known in the inspection art without necessarily achieving a full quantitative measurement or providing a visual indication thereof.

The invention claimed is:

1. In the method of measuring conductivity of nonferrous metals which includes the steps of providing a periodic signal in proximity to a conductive non-ferrous test piece to induce eddy currents therein and developing a test signal which varies as a function of said eddy currents, the improvement comprising the steps of providing a first reference signal related in phase to said periodic signal said periodic signal, said reference signal and said test signal all being at the same frequency, measuring the period of one specific test frequency at which said test signal is at a predetermined phase relationship with respect to said reference signal and determining conductivity of said non-ferrous test piece as a direct linear function of said measured period at said one specific test frequency.

2. The method set forth in claim 1 wherein the step of measuring the period of said test frequency comprises the steps of dividing said test frequency by twice a preselected scaling factor to provide a scaled output signal, providing a second periodic signal and counting periods of said second signal during a half cycle of said scaled output signal, the count during said half cycle being equal to said scaling factor multiplied by the ratio of the frequency of said second signal divided by said test frequency.

3. The method set forth in claim 2 wherein said count is scaled to a percentage of a predetermined standard conductance at a selected test frequency.

4. The method set forth in claim 3 comprising the further step of displaying said count after each said half cycle of said scaled output signal.

5. The method of measuring conductivity of nonferrous test materials having different conductivities comprising inducing eddy currents in a first nonferrous test material by means of a coil carrying a periodic signal and located in proximity to said first test material, sensing a field developed by said eddy currents to provide a test signal which varies as a function of conductivity of said first material, integrating said test signal to provide an integrated signal, providing a reference signal that is related in phase to said periodic signal, comparing said integrated signal to said reference signal to provide a difference signal which varies as a function of the difference in phase between said integrated signal and said reference signal, adjusting the frequency of said periodic signal to a first frequency at which said reference signal and said integrated signal have a preselected phase difference therebetween, and then determining conductivity of said first nonferrous test material as an inverse linear function of said first frequency.

6. The method set forth in claim 5 wherein eddy currents are induced in a second nonferrous test material by means of said coil carrying said periodic signal, a second field developed by eddy currents in said second test material is sensed to provide a second test signal which varies as a function of conductivity of said second nonferrous material, said second test signal is integrated to provide a second integrated signal, said second integrated signal is compared to said reference signal to provide a second difference signal which varies as a function of the phase difference between said second integrated signal and said reference signal, the frequency of said periodic signal is adjusted to a second frequency at which said reference signal and said second integrated signal have the same said preselected phase difference therebetween, and then conductivity of said second nonferrous material is determined as the same said inverse linear function of test frequency at said corresponding second frequency.

7. In the method of determining conductivity of test materials which includes the steps of providing a periodic signal to electromagnetically induce eddy currents in a first test material and developing a test signal which varies as a function of said eddy currents, the improvement comprising the steps of developing a reference signal as a preselected function of said periodic signal, said periodic signal, said test signal and said reference signal all being at a same test frequency, determining a relationship in phase between said test signal and said reference signal, varying said test frequency until said test frequency is at a first value at which said phase relationship is at a preselected value, and then determining conductivity of said first test material as an inverse linear function of said first value of said test frequency.

8. The method set forth in claim 7 wherein said periodic signal induces second eddy currents in a second test material and a second test signal which varies as a function of said second eddy currents is developed, and further comprising the steps of determining a second relationship in phase between said second test signal and said reference signal, varying said test frequency until said test frequency is at a second value at which said second phase relationship reaches the same said preselected value and then determining conductivity of said second test material as the same said inverse linear function of test frequency at the said corresponding second value of said test frequency.

9. The method set forth in claim 8 for determining conductivity of test materials having a predetermined minimum thickness, said test frequency being of sufficient magnitude that said induced eddy currents are substantially unrelated to material thickness.

10. The method set forth in claim 9 wherein said periodic signal is also said reference signal.

11. The method set forth in claim 7 wherein said step of determining said material conductivity comprises the steps of measuring the period of said periodic signal and displaying said measured period as a direct scaled function of said conductivity.

12. The method set forth in claim 11 wherein conductivity is displayed as a scaled percentage of a predetermined standard conductivity.

13. The method set forth in claim 7 wherein the step of determining said phase relationship comprises the steps of integrating said test signal and comparing said integrated test signal to said reference signal to develop a signal which varies as a function of a measured phase relationship therebetween.

14. The method set forth in claim 7 wherein said conductivity as so determined is digitally displayed as a direct linear function of the period of said one signal.

15. A method of measuring conductivity of non-ferrous metals having a predetermined minimum thickness which includes the steps of providing a periodic signal at one side of a conductive non-ferrous test piece to induce eddy currents therein, said periodic signal being at a test frequency which is of sufficient magnitude that said induced eddy currents are substantially unrelated to material thickness, developing a test signal at the same side of said test piece which varies as a function of said eddy currents, providing a first reference signal related in phase to said periodic signal, said periodic signal, said reference signal and said test signal all being at the same said test frequency, and determining conductivity of said non-ferrous test piece as a function of said test frequency at a predetermined phase relationship between said test signal and said reference signal.

16. The method set forth in claim 15 wherein conductivity is measured as a direct linear function of the period of said test frequency at one specific test frequency at which said test signal is at said predetermined relationship with respect to said reference signal.

17. Apparatus for measuring a characteristic of a test material comprising means providing a periodic signal including means adapted to be positioned on one side of a test material to induce eddy currents in the material, sensing means adapted to be positioned on the same said side of the test material for developing a test signal in response to said eddy currents in the material, means responsive to said periodic signal to provide a reference signal, said periodic signal, said test signal and said reference signal all being at a test frequency selected such that eddy currents induced in the test material are substantially unrelated to material thickness, means responsive to said reference signal and said test signal to provide an output according to the phase angle differential between said test signal and said reference signal, means for varying said test frequency until said test frequency is at a preselected value, and means for determining a value of said characteristic of said material as a function of said first value of said test frequency.

18. The apparatus set forth in claim 17 wherein said frequency varying means comprises means for varying the frequency of said periodic signal.

19. The apparatus set forth in claim 18 wherein said determining means comprises means measuring the period of said test frequency and means displaying said measured period as a direct scaled parameter of said characteristic.

20. The apparatus set forth in claim 19 wherein said means providing said phase differential output comprises means for integrating said test signal and means for comparing said integrated test signal to said reference signal to develop said phase differential output.

21. The apparatus set forth in claim 20 wherein said phase differential output is a direct current test signal and wherein said apparatus further comprises means providing a direct current reference representing said predetermined value of said phase differential output and means comparing said direct current test signal to said direct current reference to determine said first value of said signal parameter.

22. The apparatus set forth in claim 20 wherein said material characteristic is conductivity of a nonferrous metal and wherein said display means is calibrated to display conductivity in percent IACS.

23. The apparatus set forth in claim 19 wherein said means for measuring the period of said test frequency comprises means for dividing said test frequency by twice a preselected scaling factor to provide a scaled output signal, means for providing a second periodic signal and means for counting periods of said second periodic signal during a half cycle of said scaled output signal, the count during said half cycle being equal to said scaling factor multiplied by the ratio of the frequency of said second periodic signal divided by said test frequency.

24. Apparatus for measuring conductivity of a test material comprising means providing a periodic signal, means responsive to said periodic test signal to electromagnetically induce eddy currents in said test material, sensing means responsive to said eddy currents to develop a test signal as a function of said eddy currents, means for measuring the phase relationship between said periodic signal and said test signal, means for varying the frequency of said periodic signal until said phase relationship reaches a preselected specific level, means responsive to the period of said periodic signal to determine conductivity of the material as a direct linear function of said period when said phase relationship reaches said preselected level.

25. The apparatus set forth in claim 24 wherein said sensing means includes a plurality of coils so arranged and disposed with respect to said eddy current inducing means and said material to develop said test signal independently of effects thereon caused by said periodic signal directly.

26. The apparatus set forth in claim 24 wherein said phase relationship measuring means comprises means connected to said eddy current sensing means to electronically integrate said test signal and phase detector means for comparing said integrated test signal to said periodic signal to develop a phase differential signal proportional to the phase angle between said integrated test signal and said periodic signal.

27. The apparatus set forth in claim 26 wherein said frequency varying means comprises a voltage controlled oscillator providing said periodic signal at a frequency controlled by said differential signal.

28. The apparatus set forth in claim 24 wherein said period responsive means comprises a frequency divider for dividing the frequency of said periodic signal by twice a preselected scaling factor, a reference oscillator providing a second periodic signal at preselected frequency, a counter, and means gating said second periodic signal to said counter during a half cycle of said frequency-divided periodic signal, whereby said counter counts periods of said second periodic signal for the duration of said half cycle.

29. The apparatus set forth in claim 28 further comprising means displaying the count in said counter after each said half cycle of said frequency-divided periodic signal.

30. The apparatus set forth in claim 29 wherein said display means comprises a digital display.

31. The apparatus set forth in claim 29 wherein said display is calibrated in percentage of a predetermined standard conductivity.

32. The apparatus set forth in claim 31 wherein said percentage is proportional to said scaling factor multiplied by the ratio of said preselected reference oscillator frequency divided by said frequency of said periodic signal.

* * * * *

UNITED STATES PATENT AND TRADEMARK OFFICE
CERTIFICATE OF CORRECTION

PATENT NO. : 4,095,180
DATED : June 13, 1978
INVENTOR(S) : GORDON RALPH BROWN

It is certified that error appears in the above-identified patent and that said Letters Patent are hereby corrected as shown below:

Column 2, line 33, delete "signal" and insert --signals--.
Column 2, line 35, delete "the" (first occurrence) and insert --that--.

Column 4, line 65, delete:

$$e_{36} = -\frac{\omega M_{20/26} M_{26/22,24} I}{R_2 + (\omega L_{26})^2} \cos(\omega t - \phi)$$

and insert:

$$e_{36} = -\frac{\omega M_{20/26} M_{26/22,24} I}{R_{26}^2 + (\omega L_{26})^2} \cos(\omega t - \phi)$$

Column 5, line 28, delete "onetenth" and insert --one-tenth--.
Column 6, line 45, delete "kilohertZ" and insert --kilohertz--.
Column 10, line 1, after "signal" insert a comma (,) (first occurrence).

Signed and Sealed this

Thirteenth Day of February 1979

[SEAL]

Attest:

RUTH C. MASON
Attesting Officer

DONALD W. BANNER
Commissioner of Patents and Trademarks